United States Patent
Benedict et al.

(10) Patent No.: US 6,211,157 B1
(45) Date of Patent: Apr. 3, 2001

(54) PROTEIN MIXTURES TO INDUCE THERAPEUTIC ANGIOGENESIS

(75) Inventors: James J. Benedict, Arvada, CO (US); John P. Ranieri; Marsha L. Whitney, both of Austin, TX (US)

(73) Assignee: Sulzer Biologics, Inc., Wheatridge, CO (US)

( * ) Notice: Subject to any disclaimer, the term of this patent is extended or adjusted under 35 U.S.C. 154(b) by 0 days.

(21) Appl. No.: 09/173,989

(22) Filed: Oct. 16, 1998

Related U.S. Application Data

(60) Provisional application No. 60/083,948, filed on May 1, 1998.

(51) Int. Cl.[7] .......................... A61K 38/18; C07K 14/51; C07K 14/515
(52) U.S. Cl. .............................................. 514/21; 530/399
(58) Field of Search ........................... 530/350, 355, 530/395, 399, 412, 414, 840; 514/2, 8, 12, 21; 424/549

(56) References Cited

U.S. PATENT DOCUMENTS

| | | | |
|---|---|---|---|
| 4,529,590 | 7/1985 | LeVeen et al. | 424/95 |
| 4,699,788 | 10/1987 | Catsimpoolas et al. | 424/104 |
| 4,863,732 | 9/1989 | Nathan et al. | 424/95 |
| 4,895,838 | 1/1990 | McCluer et al. | 514/54 |
| 4,900,673 | 2/1990 | Harper et al. | 435/199 |
| 5,270,300 | 12/1993 | Hunziker | 514/12 |
| 5,290,763 | 3/1994 | Poser et al. | 514/21 |
| 5,318,957 | 6/1994 | Cid et al. | 514/8 |
| 5,328,695 | 7/1994 | Lucas et al. | 424/426 |
| 5,371,191 | 12/1994 | Poser et al. | 530/350 |
| 5,459,047 | 10/1995 | Wozney et al. | 435/69.1 |
| 5,470,831 | 11/1995 | Whitman et al. | 514/16 |
| 5,543,394 | 8/1996 | Wozney et al. | 514/12 |
| 5,631,142 | 5/1997 | Wang et al. | 435/69.1 |
| 5,635,372 | 6/1997 | Celeste et al. | 435/69.1 |
| 5,637,480 | 6/1997 | Celeste et al. | 435/69.4 |
| 5,661,007 | 8/1997 | Wozney et al. | 435/69.4 |
| 5,703,043 | 12/1997 | Celeste et al. | 514/12 |
| 5,728,679 | 3/1998 | Celeste et al. | 514/12 |
| 5,846,770 | 12/1998 | LaVallie et al. | 435/69.1 |
| 5,849,880 | 12/1998 | Wozney et al. | 530/399 |
| 5,854,207 | 12/1998 | Lee et al. | 514/2 |
| 5,866,364 | 2/1999 | Israel et al. | 435/69.1 |
| 5,902,785 | 5/1999 | Hattersley et al. | 514/2 |
| 5,932,216 | 8/1999 | Celeste et al. | 424/158.1 |
| 5,965,403 | 10/1999 | Celeste et al. | 435/69.4 |
| 5,972,884 | 10/1999 | Cohen et al. | 514/12 |

OTHER PUBLICATIONS

J. Folkman, MD; *Angiogenic Therapy of the Human Heart*; Circulation 1988; (pp.628–629).

B. Schumacher, MD;, et al; *Induction of Neoangiogenesis in Ischemic Myocardium by Human Growth Factors*; Circulation; 1988; (pp.645–650).

Takashi Nakaoka, et al; *Inhibition of Rat Vascular Smooth Muscle Proliferation in Vitro and in Vivo by Bone Morphogenetic Protein–2*; Journal of Clinical Investigation; vol. 100, No. 11, Dec. 1997; (pp. 2824–2832).

Hidetoshi Yamashita, et al; *Growth/Differentiation Factor–5 Induces Angiogenesis in Vivo*; Exp. Cell Res. 1997; (pp. 218–226).

J. P. Levine, M.D. et al; *Bone Morphogenetic Protein Promotes Vascularization and Osteoinduction in Preformed Hydroxyapatite in the Rabbit*; Ann. Plast. Surg. 1997; (pp. 158–168).

*Primary Examiner*—Jeffrey E. Russel
(74) *Attorney, Agent, or Firm*—Timothy L. Scott; Philip S. Lyren; Kenneth S. Barrow

(57) ABSTRACT

An angiogenic factor comprising a mixture of proteins derived from bone. The angiogenic protein mixture is produced by a series of steps that allow the proteins to be kept in solution. The angiogenic mixture of bone proteins is produced by a multi-step process that includes at least one ultrafiltration step, an anion exchange chromatography step, a cation exchange chromatography step and a high performance liquid chromatography (HPLC) purification step.

22 Claims, 3 Drawing Sheets

(2 of 3 Drawing Sheet(s) Filed in Color)

SDS – POLYACRYLAMIDE GEL OF PROTEINS FROM HPLC

Figure 2. Quail Chorioallantoic Membrane (CAM) Angiogenesis Assay
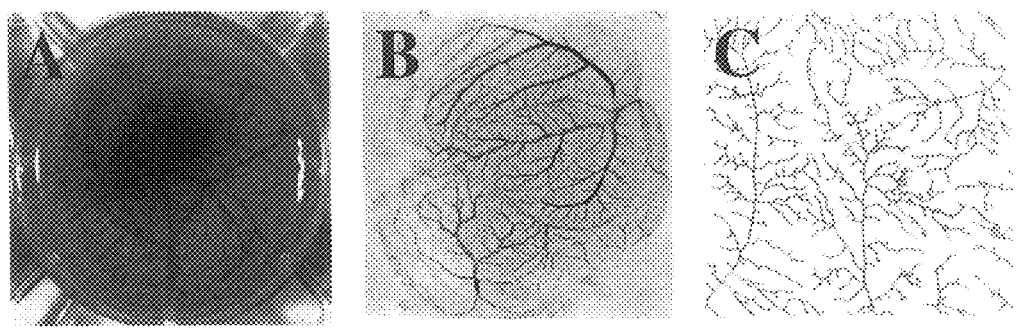
Figure 3. Black and white images of CAM vasculature after growth factor treatment
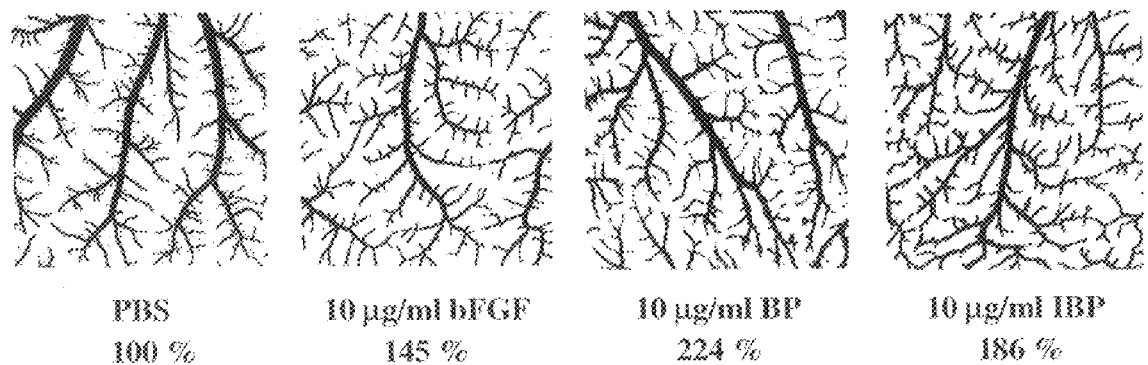
| PBS | 10 µg/ml bFGF | 10 µg/ml BP | 10 µg/ml IBP |
| 100 % | 145 % | 224 % | 186 % |

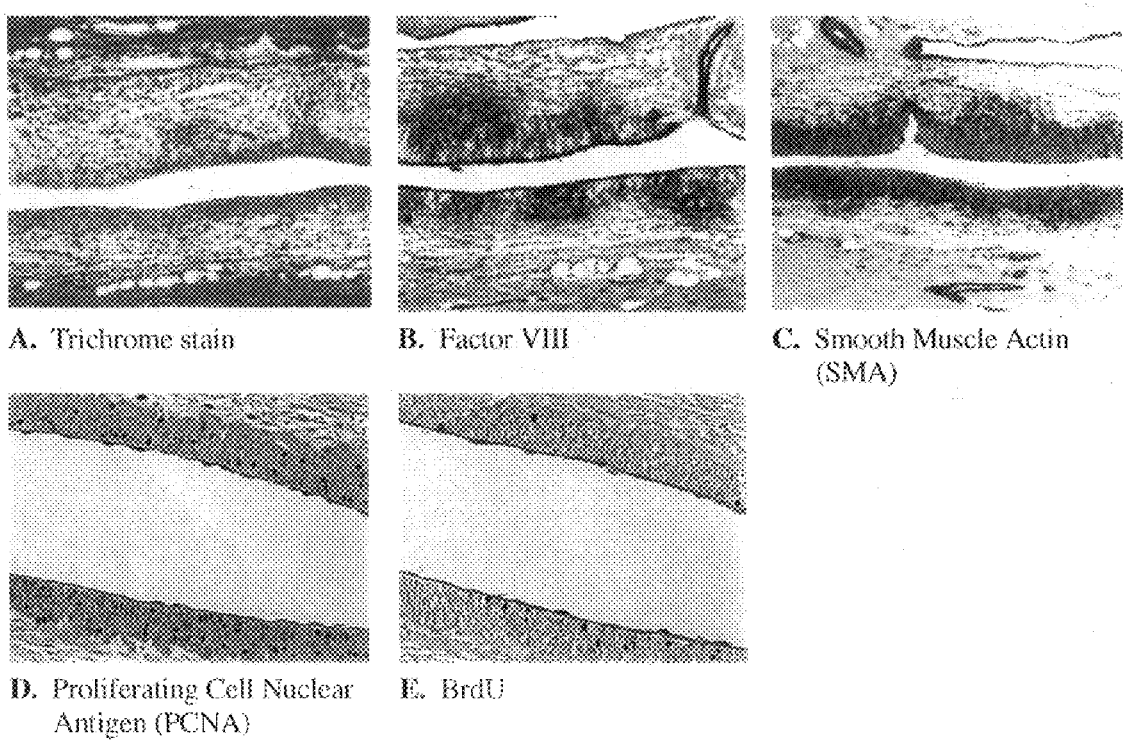
Figure 4. Histological sections of blood vessels formed in canine myocardium 2 weeks following BP injection
A. Trichrome stain
B. Factor VIII
C. Smooth Muscle Actin (SMA)
D. Proliferating Cell Nuclear Antigen (PCNA)
E. BrdU

PROTEIN MIXTURES TO INDUCE THERAPEUTIC ANGIOGENESIS

This application claims benefit from U.S. Provisional Application Ser. No. 60/083,948 filed May 1, 1998.

FIELD OF THE INVENTION

The present invention relates to a method for inducing the growth of blood vessels in instances where it is desirable to increase the supply of blood to a portion of a living body. More particularly, the present invention comprises a novel angiogenic factor. Still more particularly, the present invention relates to the use of mixtures of protein extracted from bone to cause therapeutic angiogenesis.

BACKGROUND OF THE INVENTION

There are many medical circumstances in which an increase in the supply of blood to living tissue is indicated. These include: burns and wound healing, in which the incorporation of angiogenic factors into artificial skin may facilitate the formation of blood vessels in the healing wound and reduce the risk of infection; cardiovascular disease, in which repair of anginal or ischemic cardiac tissue can be effected by causing the ingrowth of new blood vessels; stroke, where increased blood supply to the brain can reduce the risk of transient ischemic attack and/or cerebral arterial deficiency; and peripheral vascular disease, in which blood flow in the extremities is diminished. In each case, it is believed that the growth of new blood vessels will increase the volume of blood circulating through the tissue in question, and correspondingly increase the amount of oxygen and nutrients available to that tissue.

Atherosclerosis is a major cause of cardiovascular disease, stroke and peripheral vascular disease. Atherosclerosis affects the blood vessels, including those of the heart. This disease may have its beginnings early in life and is first noted as a thickening of the arterial walls. This thickening is an accumulation of fat, fibrin, cellular debris and calcium. The resultant narrowing of the lumen of the vessel is called stenosis. Vessel stenosis impedes and reduces blood flow. Hypertension and dysfunction of the organ or area of the body that suffers the impaired blood flow can result. As the buildup on the inner wall of a vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

Small vessels, such as the arteries that supply blood to the heart, legs, intestines and other areas of the body, are particularly susceptible to atherosclerotic narrowing. When an artery in the leg or intestine is affected, the resultant loss of blood supply to the leg or segment of the intestine may result in gangrene. Atherosclerotic narrowing of one or more of the coronary arteries limits and in some instances prevents blood flow to portions of the heart muscle. Depending upon the severity of the occlusion and its location within the coronary circulation system, pain, cardiac dysfunction or death may result.

In many instances, it is possible to correct aneurysms and stenosis of major arteries using plastic reconstruction that does not require any synthetic graft or patch materials. In other instances, such as where the disease is extensive and the vessel is no longer reliable, the blocked or weakened portion of the vessel is usually replaced with a graft. In such case, the involved vessel section is transected and removed and a synthetic patch, conduit or graft is sewn into place. These types of procedures, including coronary artery bypass grafting (CABG) and percutaneous transluminal coronary angioplasty (PTCA), are routinely performed for the purpose of alleviating ischemia.

Nevertheless, coronary artery disease alone is responsible for approximately 550,000 deaths each year in the United States. Peripheral vascular disease results in lower limb amputation in about 150,000 patients each year, with a subsequent mortality rate of 40% within two years of amputation. Some of the difficulty in treating arterial occlusion may lie in the fact that each of these surgical procedures is associated with a certain incidence of restenosis and may not be appropriate in certain instances. This is particularly true when the patient is elderly or has undergone a previous CABG or PTCA procedure. Furthermore, in such cases, a less invasive technique is preferred.

It is believed, therefore, that stimulation of blood vessel growth into the affected region will provide the desired effect and will avoid many of the disadvantages associated with bypass surgery. While angiogenic factors in general have been the subject of much research, no angiogenic factor has yet been found to produce results that are entirely satisfactory. Examples of such growth factors are transforming growth factor beta (TGF-β), osteonectin or SPARC, platelet-derived growth factor (PDGF), basic fibroblast growth factor (bFGF) and vascular endothelial growth factor (VEGF). All of these growth factors are either synthetic, meaning they are manufactured chemically from non-living sources, or are produced by recombinant manufacturing processes. Each of these angiogenic factors comprises only a single protein and are possesses only a single functionality. In addition, many of the known angiogenic compounds are exceedingly difficult and/or expensive to manufacture.

Hence, it is desired to provide an effective angiogenic factor that is easy to manufacture from readily available materials, easily administered by the surgeon and effective at stimulating the growth of new blood vessels into the treated tissue.

BRIEF SUMMARY OF THE INVENTION

The present invention comprises an angiogenic factor that is easily manufactured from readily available materials, easily administered by the surgeon and effective at stimulating the growth of new blood vessels into the treated tissue. The angiogenic factor of the present invention comprises a group of proteins extracted from bone. It has been found that the mixtures of proteins produced by certain processes are particularly effective angiogenic agents. These angiogenic agents can be administered as part of the treatment of an existing vascular disorder, or can play a role in early intervention and prevention if administered in certain cases.

According to the present invention, a mixture of bone proteins having a surprising degree of angiogenic activity is produced by a multi-step process that includes at least one ultrafiltration step, an anion exchange chromatography step, a cation exchange chromatography step and a high performance liquid chromatography (HPLC) purification step.

BRIEF DESCRIPTION OF THE DRAWINGS

This file of this patent contains at least one drawing executed in color. Copies of this patent with color drawing (s) will be provided by the Patent and Trademark Office upon request and payment of the necessary fee.

For a more detailed description of the present invention, reference will now be made to the accompanying Figures, wherein:

FIGS. 2A–C show the results of a quail chorioallantoid membrane (CAM) angiogenesis assay of a protein mix according to the present invention;

FIGS. 3 show the vascular growth in the CAM of FIGS. 2; and

FIGS. 4A–E are histological sections of blood vessels formed in the canine myocardium following treatment with a protein mix in accordance with the present invention.

DETAILED DESCRIPTION OF THE PREFERRED EMBODIMENTS

Figure 1:
FIG. 1 illustrates an SDS-PAGE of one embodiment of the present angiogenic protein mixture, both in reduced and non-reduced forms.

Angiogenesis is a complex process involving several different cell types and molecular signaling events. Endothelial cells must secrete proteases to dissolve cell-cell and cell-matrix attachments, migrate and proliferate to form new vascular branches. Although single factors such as bFGF and VEGF have shown promise as angiogenic agents, a more robust angiogenic response may be obtained through the use of an agent that comprises a mixture of proteins. This may be due in part to a synergistic effect of the combined proteins on the subject tissue. According to a preferred embodiment, an angiogenic mixture of bone proteins is produced by a multi-step process that includes an ultrafiltration step, an anion exchange chromatography step, a cation exchange chromatography step and a high performance liquid chromatography (HPLC) purification step.

While preferred processes for producing the angiogenic protein mixtures of the present invention are described in full detail in U.S. Pat. Nos. 5,290,763 and 5,371,191, which are incorporated herein in their entireties, the process can be summarized as follows. In a first step, demineralized bone particles from a suitable source (such as crushed bone) are subjected to protein extraction using guanidine hydrochloride. The extract solution is filtered, and subjected to a two step ultrafiltration process. In the first ultrafiltration step, an ultrafiltration membrane having a nominal molecular weight cut off (MWCO) of 100 kD is preferably employed. The retentate is discarded and the filtrate is subjected to a second ultrafiltration step using an ultrafiltration membrane preferably having a nominal MWCO of about 10 kD. The retentate is then subjected to diafiltration to substitute urea for guanidine. The protein-containing urea solution is then subjected to sequential ion exchange chromatography, first anion exchange chromatography followed by cation exchange chromatography. For the anion exchange process, a strongly cationic resin is used, preferably having quaternary amine functional groups. Typically, the eluant for the anion exchange process has a conductivity from about 10,260 micromhos ($\mu$mhos) (1.026×10<-2>siemens (S)) to about 11,200 $\mu$mhos (1.120×10<31 2>S). For the cation exchange process, a strongly anionic resin is used, preferably having sulfonic acid functional groups. The eluant for the cation exchange process typically has a conductivity from about 39,100 $\mu$mhos (3.91×10<-2>S) to about 82,700 $\mu$mhos (8.27×10<-2>S) or more.

In the process described above, the proteins are advantageously kept in solution. According to the present invention, the proteins produced by the above process are then subjected to HPLC. The HPLC process preferably utilizes a column containing hydrocarbon-modified silica packing material. The osteoinductive proteins can be loaded onto the HPLC column in a solution of aqueous trifluoracetic acid or other suitable solvent, such as heptafluorobutyric acid, hydrochloric or phosphoric acid. Preferably, a trifluoracetic acid solution having a concentration of from about 0.05 percent by volume to about 0.15 percent by volume, and more preferably about 0.1 percent by volume trifluoracetic acid is used.

Proteins are eluted from the HPLC column with an organic solvent/water mixture suitable for obtaining the desired proteins. A preferred eluant in the HPLC process is an acetonitrile solution. The preferred eluant typically has an acetonitrile concentration which varies, during elution, from about 30 percent by volume to about 45 percent by volume. In preferred embodiments, the acetonitrile concentration in the eluant is increased in increments of between about 0.30 percent by volume and about 0.40 percent by volume per minute until the desired highest concentration of acetonitrile is achieved. Proteins can be recovered from the HPLC process eluant by means generally known in the art. A preferred angiogenic fraction of the eluted proteins occurs when the actonitrile concentration in the eluant is between about 33 percent by volume and about 37 percent by volume.

The purification processes described above yield novel angiogenic protein mixtures. Because they comprise mixtures of proteins, these angiogenic factors are most easily described in terms of their properties. Hence, in one embodiment of the present angiogenic factor, the factor is a mixture of a number of proteins having the sodium dodecyl sulfate polyacrylamide gel electrophoresis (SDS-PAGE) profile shown in FIG. 1.

Another characterization of the present invention is a mixture of proteins having a preferred amino acid composition of about 20–25 mole percent of acidic amino acids [ASP(+ASN) and GLU(+GLN)]; about 10–15 mole percent of hydroxy amino acids (SER and THR); about 35–45 mole percent aliphatic amino acids (ALA, GLY, PRO, MET, VAL, ILE, and LEU); about 4–10 mole percent aromatic amino acids (TYR and PHE); and about 10–20 mole percent basic amino acids (HIS, ARG and LYS). More particularly, the angiogenic protein mixture amino preferably has an amino acid composition of about 23.4 mole percent of acidic amino acids [ASP(+ASN) and GLU(+GLN)]; about 13.5 mole percent of hydroxy amino acids (SER and THR); about 40.0 mole percent aliphatic amino acids (ALA, GLY, PRO, MET, VAL, ILE, and LEU); about 6.8 mole percent aromatic amino acids (TYR and PHE); and about 16.6 mole percent basic amino acids (HIS, ARG and LYS). (TRP, CYS and ½ CYS were not measured and are not included in the calculation of mole percent.)

An alternative embodiment of the present angiogenic factor can be defined as a different fraction of the total protein stream exiting the HPLC process. More particularly, the proteins eluted when the eluant has an acetonitrile concentration of from about 37 to about 39.5 percent by volume have been found to have surprising angiogenic activity. The mixture defined in this manner contains hundreds of natural proteins. It is believed that the angiogenic activity of proteins obtained in this manner may be further enhanced by selecting smaller fractions of the eluant and quantitatively comparing the angiogenic activity of each fraction.

The bone-derived angiogenic protein (BDAP) mixture produced in accordance with the present invention is preferably administered directly to ischemic tissue in a suitable carrier. For example, in some instances, it may be desired to apply the angiogenic factor in a carrier that allows it to be absorbed quickly, while in other instances it may be desired to apply the angiogenic factor in a controlled, time-release manner. In other instances, a single dose or other variation may be preferred. In general, the preferred carrier material will vary depending on the desired clinical application or site of administration. Polylactic acid, polyglycolic acid and their copolymers, collagen, PLURONIC® (polyoxyalkylene ether co-polymer surfactant), and povidone (polyvinylpyrrolidone) are all examples of biocompatible materials that can be combined with BDAP mixtures to stimulate angiogenesis.

EXAMPLE 1

Quail chorioallantoic membrane (CAM) was in the manner described in "A Novel Assay of Angiogenesis in the Quail Chorioallantoic Membrane: Stimulation by bFGF and Inhibition by Angiostatin According to Fractal Dimension and Grid Intersection," (Parsons-Wingerter P., Dwai B., Yang M C., Elliot K E., Milaninia A., Redlitz A., Clark J. and Sage E. H. Fertilized Japanese quail eggs (*Cotumix cotumix japonica*) were opened onto Petri dishes on day 3 post-incubation (FIG. 2A). After 4 days of culture, a BDAP mixture, diluted in PBS/ovalubumin prewarmed to 37° C., was distributed evenly onto the surface of the CAM. After 24 hours of incubation, the CAM's were fixed, dissected and photographed (FIG. 2B) at 10× magnification to visualize the arterial vascular tree, including endstage vessels. Digital images of triplicate CAM specimens were acquired at 10× magnification in grayscale, binarized to black-and-white, and skeletonized (FIG. 2C). The vessel branching pattern was analyzed and quantified by the fractal dimension.

The photographs in FIG. 3 are representative digital binarized images of CAMs exposed to 10 $\mu$g/ml dose of growth factor for 24 hours. Quantitative data corresponding to these images were acquired by analyzing the skeletonized images and determining the fractal dimension of the branched vascular pattern. Data were pooled from two separate experiments consisting of three CAMs per experiment. Exposure to BDAP resulted in 124% greater mean angiogenic stimulation over the basal rate (defined as the change in fractal dimension in untreated controls) versus a 43% increase over basal rate for bFGF-treated CAMs. (p<0.006).

It is hypothesized that this combination of factors acts synergistically to facilitate the proliferation, migration and differentiation processes essential to angiogenesis more effectively than a single factor.

Preliminary data suggest that other fractions of proteins eluted from bone are also angiogenic. An assay of a second protein mixture, BDAP-2, defined as the fraction eluting at an acetonitrile concentration of from about 37 to about 39.5 percent, membrane was performed on quail chorioallantoic membrane (CAM) using the same protocol as that described above with respect to the BDAP assay. The angiogenic response in the quail CAM assay was 86 percent greater than the basal angiogenic rate after treatment with this alternative protein mix.

Canine Myocardial Angiogenesis Pilot Study

Four adult mongrel dogs of either sex, weighing 21–26 kg, were anesthetized and a left thoracotomy performed through the fifth intercostal space. All visible epicardial collaterals connecting LAD diagonals to circumflex or right coronary arteries were ligated to minimize collateral flow to the LAD territory and an ameroid constrictor was placed on the proximal to the first diagonal branch. After completing the procedure, 0, 10 or 100 $\mu$g BDAP was injected in a 0.1 cc volume of povidone (polyvinylpyrrolidone), as polymer microspheres suspended in povidone, or in collagen gel for a total of nine injections. Each series of injections was administered in the ischemic LAD region of the left ventricle, as well as in a non-ischemic LCX region. The chest was closed and the animal was allowed to recover.

In order to provide an index of cellular proliferation at multiple time points after the initial surgery, bromodeoxyuridine (BrdU, 25 mg/kg, Sigma, St. Louis, Mo.) was administered subcutaneously on post-operative days 2, 4, 6, 8, 10, 12, 14 and 21. After two or six weeks, the dogs were euthanized and the hearts explanted and cut into samples. Samples were fixed and serial sections, 4–5 microns thick, were cut and stained with Masson's trichrome stain to evaluate the general morphology of the myocardium. Sister sections were stained using standard immunohistochemical techniques with antibodies against bromodeoxyuridine (BrdU), PC10 proliferating cell nuclear antigen (PCNA), alpha smooth muscle actin (SMA) and Factor VIII using standard techniques.

Initial histological data (FIGS. 4A–E) indicate that 10 or 100 micrograms of BDAP suspended in 0.1 cc povidone stimulated blood vessel formation within two weeks post injection. Whereas control sections showed no significant vessel formation and the needle tract was visible, BDAP-treated sections had several newly formed blood vessels, as evidenced by Masson's trichrome staining (FIG. 4A). Immunohistochemical staining demonstrated that these vessels are lined with endothelial cells (dark stain FIG. 4B) and surrounded by a layer of smooth muscle cells (brown stain FIG. 4C). PCNA- and BrdU-stained sections (FIGS. 4D–E) indicated that these vascular endothelial and smooth muscle cells are actively proliferating. Thus, based on the qualitative results of the canine study, it was concluded that BDAP stimulates formation of new differentiated blood vessels approximately 50–100 $\mu$m in diameter in canine myocardium. (Note, in FIG. 4AC, 1 cm≈200 $\mu$m; in FIG. 4D–E, 1 cm≈40 $\mu$m).

Administration of angiogenic factors in accordance with the present invention has several advantages over the alternative methods for inducing angiogenesis, such as inflammation resulting from laser injury. The growth factors of the present invention can be delivered in a minimally invasive manner to ischemic tissues either through a thoracotomy or percutaneous catheterization without the use of expensive equipment. In addition, the process for manufacturing the present angiogenic factors can be readily scaled up to a commercial production scale. A further advantage is that the proteins are kept in solution during the purification steps and exhibit little deterioration during the production process. Another advantage is that the resultant mixture of proteins can be used directly, without the mixing that may be required with proteins produced by other processes.

While the present angiogenic factor and methods for producing and administering it have been described according to a preferred embodiment, it will be understood that departures can be made from some aspects of the foregoing description without departing from the scope of the invention.

What is claimed is:

1. A method for inducing angiogenesis, comprising:
   delivering a mixture of proteins derived from ground bone to an ischemic living tissue in a patient in need of angiogenesis.

2. The method according to claim 1 wherein said bone-derived protein mixture has a sodium dodecyl sulfate polyacrylamide gel electrophoresis (SDS-PAGE) profile comprising substantially all of the protein bands shown in FIG. 1.

3. The method according to claim 1 wherein said bone-derived protein mixture has an amino acid composition of about 20–27 mole percent of acidic amino acids, about 10–15 mole percent of hydroxy amino acids, about 35–45 mole percent aliphatic amino acids, about 4–10 mole percent aromatic amino acids, and about 10–20 mole percent basic amino acids.

4. The method according to claim 1 wherein said bone-derived protein mixture comprises a fraction of a total protein stream eluted from ground, demineralized, ion-exchanged bone in an HPLC column.

5. A method for inducing angiogenesis, comprising:
   administering a mixture of bone-derived protein to a living tissue to cause angiogenesis in a patient in need of angiogenesis,
   wherein said angiogenesis is not included in a process for bone growth.

6. The method according to claim 5 wherein said bone derived protein mixture has a sodium dodecyl sulfate polyacrylamide gel electrophoresis (SDS-PAGE) profile comprising substantially all of the protein bands shown in FIG. 1.

7. The method according to claim 5 wherein said bone derived protein mixture has an amino acid composition of about 20–27 mole percent of acidic amino acids, about 10–15 mole percent of hydroxy amino acids, about 35–45 mole percent aliphatic amino acids, about 4–10 mole percent aromatic amino acids, and about 10–20 mole percent basic amino acids.

8. The method according to claim 5 wherein said bone-derived protein mixture comprises a fraction of a total protein stream eluted from ground, ion-exchanged bone in an HPLC column.

9. A method for stimulating blood vessel growth, comprising:
   injecting a mixture of proteins in soft tissue in a patient in need of angiogenesis,
     wherein said mixture is produced by a process comprising:
     (i) subjecting a first solution containing demineralized bone to ultrafiltration to obtain a second solution;
     (ii) loading said second solution onto an anion exchange resin;
     (iii) eluting proteins from said anion exchange resin with a first eluant to obtain an anion exchanged fraction eluate;
     (iv) loading said anion exchanged fraction eluate onto a cation exchange resin;
     (v) eluting proteins from said cation exchange resin with a second eluant to obtain a cation exchanged fraction eluate;
     (vi) loading a solution of proteins from said cation exchanged fraction eluate onto a reverse phase HPLC column; and
     (vii) eluting proteins from said HPLC column with a third eluant.

10. The method according to claim 9 wherein step (vii) is carried out with an eluant having a gradient of increasing acetonitrile concentration ranging from about 30 percent volume to about 40 percent by volume.

11. The method according to claim 9 wherein the eluant of step (vii) comprises a trifluoracetic acid solution having a concentration of from about 0.05 percent by volume bout 0.15 percent by volume.

12. The method according to claim 9 wherein step (vii) results in a purified angiogenic protein mixture.

13. The method according to claim 9 wherein the second solution contains proteins having a molecular weight of less than about 100 kD.

14. The method cording to claim 1, wherein said delivering comprises delivering through a thoracotomy.

15. The method according to claim 1, wherein said delivering comprises delivering through a percutaneous catheterization.

16. The method according to claim 1, wherein said delivering comprises injecting.

17. A method for inducing angiogenesis, comprising:
   delivering a mixture of proteins derived from ground bone to an ischemic living tissue in need of angiogenesis.

18. A method for inducing angiogenesis, comprising:
   administering mixture of bone-derived protein to a living tissue in need of angiogenesis,
   wherein said angiogenesis is not included in a process for bone growth.

19. A method for string blood vessel growth, comprising:
   injecting a mixture of proteins in soft tissue in need of angiogenesis,
   wherein the proteins are derived from ground bone.

20. A method for inducing angiogenesis, comprising:
   administering a mixture of bone-derived protein to a living tissue in a patient in need of angiogenesis,
   wherein said administration is not included in a process for bone growth.

21. A method for inducing angiogenesis, comprising:
   administering a mixture of bone-derived protein to a living tissue in a patient in need of angiogenesis,
   wherein said administration is carried out in the absence of a carrier that supports bone growth.

22. A method for inducing angiogenesis, comprising delivering a mixture of proteins derived from ground bone to an ischemic living tissue where bone growth is not desired.

* * * * *